US009243996B2

(12) United States Patent
Van Praet

(10) Patent No.: US 9,243,996 B2
(45) Date of Patent: Jan. 26, 2016

(54) LED DENSITOMETER FOR MICROTITER PLATE

(75) Inventor: Peter Van Praet, Haasrode (BE)

(73) Assignee: Gold Standard Diagnostics, Davis, CA (US)

(*) Notice: Subject to any disclaimer, the term of this patent is extended or adjusted under 35 U.S.C. 154(b) by 909 days.

(21) Appl. No.: 13/383,986

(22) PCT Filed: Jul. 16, 2010

(86) PCT No.: PCT/US2010/002012
§ 371 (c)(1),
(2), (4) Date: Mar. 22, 2012

(87) PCT Pub. No.: WO2011/008299
PCT Pub. Date: Jan. 20, 2011

(65) Prior Publication Data
US 2012/0182556 A1    Jul. 19, 2012

(30) Foreign Application Priority Data
Jul. 16, 2009 (BE) .................................. 2009/00434

(51) Int. Cl.
*G01N 21/00* (2006.01)
*G01N 21/25* (2006.01)

(52) U.S. Cl.
CPC .............. *G01N 21/00* (2013.01); *G01N 21/253* (2013.01); *G01N 2201/0446* (2013.01); *G01N 2201/0453* (2013.01); *G01N 2201/0627* (2013.01); *G01N 2201/10* (2013.01)

(58) Field of Classification Search
CPC ..... G01N 21/25; G01N 21/255; G01N 21/272
USPC ................................... 356/440, 244, 246, 73;
250/227.22–227.24, 205
See application file for complete search history.

(56) References Cited

U.S. PATENT DOCUMENTS 5,206,568 A * 4/1993 Bjornson ............. G01N 21/253
318/568.1
6,097,025 A * 8/2000 Modlin ................ G01N 21/253
250/205

* cited by examiner

*Primary Examiner* — Gregory J Toatley
*Assistant Examiner* — Iyabo S Alli
(74) *Attorney, Agent, or Firm* — Heisler & Associate

(57) ABSTRACT

Light emitting diodes (LEDs) are mounted in an array to an upper structure overlying a lower structure with a plurality of light detectors thereon. Each LED is configured to overlie a separate detector. Each LED emits light at a frequency relevant for measuring optical density of a specimen. LEDs having different frequencies are included within the LED array. A corresponding array of detectors is also provided, mounted to the lower structure. Spacing between adjacent LEDs and between adjacent detectors match a spacing between wells in a microtiter plate. Spacing between the lower structure and the upper structure supporting the LEDs is sufficient for the microtiter plate to fit between. Circuitry sequentially fires individual LEDs and gathers optical density data through the detectors for specimens in the wells of the microtiter plate. The structures are then moved to a next adjacent well position on the microtiter plate and the process repeated.

21 Claims, 3 Drawing Sheets

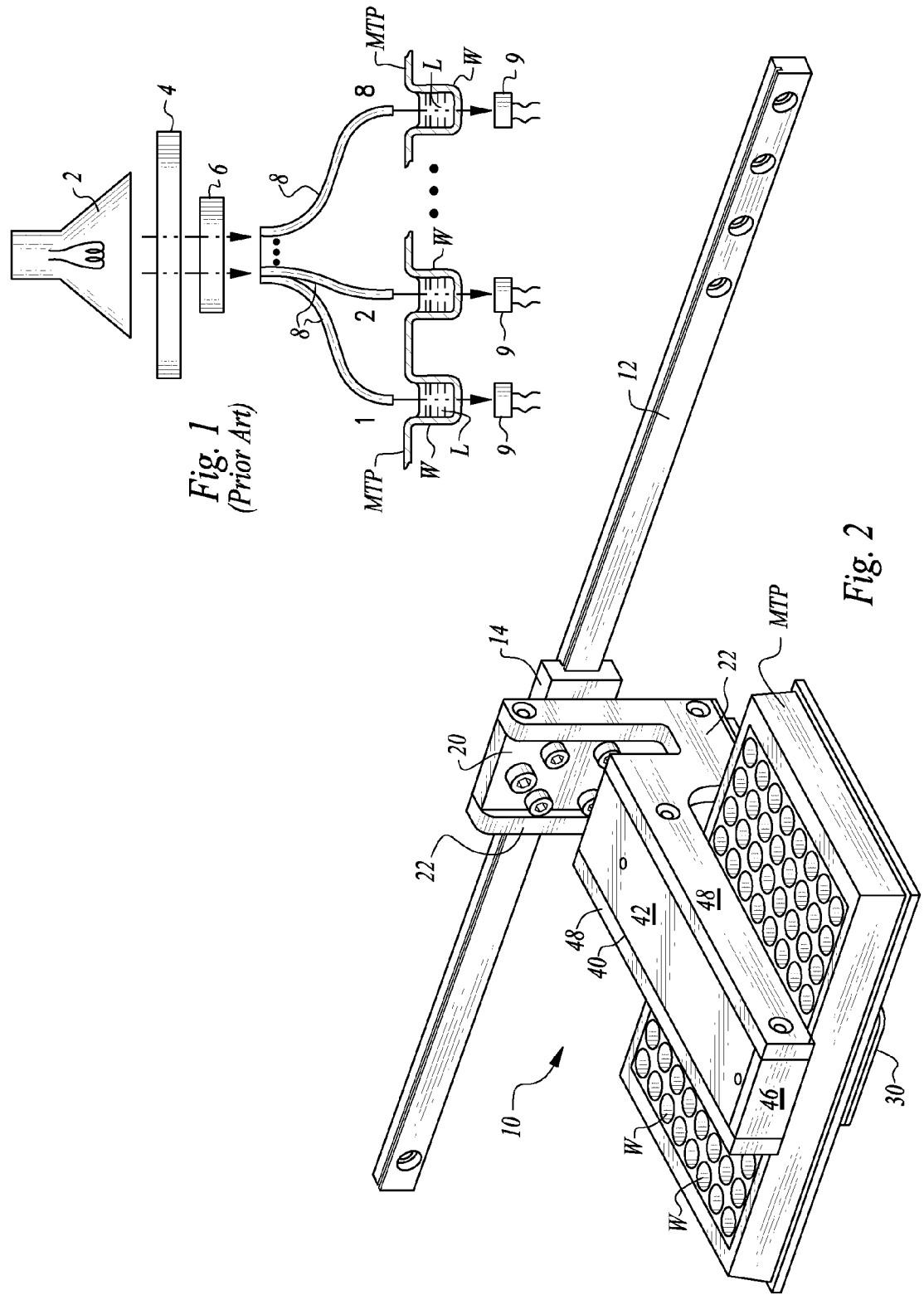

LED DENSITOMETER FOR MICROTITER PLATE

CROSS-REFERENCE TO RELATED APPLICATIONS

This application claims benefit of the earlier filing dates associated with International Patent Application No. PCT/US2010/002012 filed on Jul. 16, 2010, which designates the United States and other countries; and BE 2009/0434 filed on Jul. 16, 2009 which was claimed for priority in the above-identified international application.

FIELD OF THE INVENTION

The following invention relates to densitometers for measuring the optical density of fluids, such as in the medical diagnostic field. More particularly, this invention relates to densitometers which measure optical density of multiple specimens, such as those within wells of a microtiter plate (MTP) at more than one wavelength, such as for Enzyme Immuno Assay (EIA) tests or Enzyme Linked Immuno Sorbent/Immuno-Sorption Assay (ELISA) tests.

BACKGROUND OF THE INVENTION

Densitometry is a field where the optical density of a fluid specimen is measured by providing a light source and a detector with the detector detecting the amount of light transmitted through the specimen. In more advanced forms of densitometry, the light is limited to a narrow band of light frequencies. Multiple densitometer readings are obtained at different light frequencies to learn more about the specimen being examined.

To efficiently analyze multiple specimens as quickly and reliably as possible, a microtiter plate is often utilized with a plurality of wells therein arranged in rows and columns. The microtiter plate is substantially planar and is typically oriented substantially horizontally to keep the specimens within the wells of the microtiter plate MTP. One such arrangement of microtiter plate is shown in FIG. 2.

Furthermore, to efficiently analyze specimens within separate wells of the microtiter plate, a single light source can be divided through known prior art equipment into separate light sources, such as through the use of fiber optic light conductors each feeding a single light source to multiple separate wells. Using known prior art equipment, such as that depicted in FIG. 1, a single light source such as a halogen lamp 2 is provided. An infrared filter 4 can be utilized to remove infrared portions of the spectrum, to remove heat containing portions of the spectrum from the light being emitted from the lamp 2. An interference filter 6 is utilized to absorb all light frequencies other than those particularly desired for a measurement being conducted by the densitometer. In some more advanced systems, multiple interference filters 6 are provided which can be selectively positioned in line with the lamp 2 so that different frequencies of light are allowed to pass onto the light conductors 8.

Detectors 9 are provided below the wells in the microtiter plate MTP so that the liquid L contained within the wells W is separately measured by the detectors 9. Typically, the interference filter 6 limits the wavelength to −5 to +5 nanometers of the desired wavelength. Depending on the nature of the liquid L, more or less of the light is absorbed. Under the well W, the non-absorbed light is captured and conducted to the detector 9. The luminous intensity is measured and the absorption can be calculated. Multiple wells W are measured simultaneously with such prior art densitometers, so that the densitometer can act multiple times faster depending on the number of light conductors 8 utilized and the size of the microtiter plate MTP.

While generally effective, one problem with such densitometers is the potential for light from adjacent light conductors to have some influence on the luminous intensity read by each detector, such that otherwise properly calibrated detectors might detect a greater intensity than is actually passing through the specimen because it is hitting the detector at least partially from one of the other light conductors. Furthermore, with the prior art multiple interference filters are required and mechanisms for adjusting the interference filters so that proper frequency light is utilized for the particular densitometer test being conducted. These details add complexity to the densitometer and slow down the process Accordingly, a need exists for further enhancement of the efficiency and reliability of densitometer systems and methods.

SUMMARY OF THE INVENTION

With this invention a densitometer is provided which can perform multiple densitometer readings both at singular light frequencies and at different light frequencies for each position of the densitometer relative to a specimen support such as a microtiter plate (MTP). The densitometer includes a lower structure such as in the form of a lower plate and an upper structure such as in the form of a housing. One of these structures includes a plurality of detectors thereon with the other of these structures including a plurality of light emitting diodes (LEDs) thereon. Preferably the lower structure is in the form of a detector plate with a plurality of detectors thereon and the upper structure is in the form of the housing with the plurality of LEDs thereon.

The detectors and LEDs are preferably provided in arrays which match each other with a similar number of rows and columns of LEDs and detectors. Each LED is aligned with a corresponding detector substantially vertically. Spacing between adjacent LEDs and spacing between adjacent detectors is preferably similar to spacing between wells in a microtiter plate (MTP) so that a plurality of wells can be interposed between sets of LEDs and detectors for substantially simultaneous detection, or rapid sequential detection without movement of the microtiter plate (MTP) relative to the upper and lower structures of the densitometer.

Some of the LEDs such as each LED in a common column, preferably have a common frequency of light emitted thereby. Preferably, LEDs in separate columns emit light at differing frequencies, such that within a given row, each LED has a different frequency of light being emitted. The detectors can be similar to each other or, if needed, can be optimized for particular light frequencies and hence be different from each other.

The housing or other upper structure and detector plate or other lower structure are fixed together and spaced apart by a distance sufficient to allow a specimen supporting structure such as the microtiter plate (MTP) to pass between the upper structure and lower structure of the densitometer. The entire densitometer is carried in a movable fashion such as by being mounted to a carriage sliding upon a rail, so that the densitometer can move relative to the microtiter plate (MTP). Optionally, the microtiter plate can also be configured to move.

When using the invention, the densitometer would first be positioned with the various LEDs aligned over wells in the microtiter plate. Then, individual LEDs would be sequentially caused to emit light and associated detectors would measure luminous intensity transmitted through specimens in associated wells of the microtiter plate. Such data would then be processed, such as by storage in a database and correlated to the particular well in the microtiter plate. After each of the LEDs has been illuminated and an appropriate detection made by detectors associated with each LED, the entire densitometer can then be moved one well over and the complete process repeated. In this way, each well in the microtiter plate (MTP) is exposed to a different frequency of light and appropriate data is collected. A number of LEDs in each column determines how many samples can be simultaneously processed. The number of rows in the array of LEDs determines the number of separate frequencies of light which can provide separate data for the densitometer analysis.

OBJECTS OF THE INVENTION

Accordingly, a primary object of the present invention is to provide a densitometer which can measure optical density rapidly for a large number of specimens and provide accurate optical density data at a variety of different frequencies.

Another object of the present invention is to provide an optical density densitometer which works with a microtiter plate (MTP) and which exhibits a high duty cycle.

Another object of the present invention is to provide a method for measuring optical density of a plurality of liquid specimens in a rapid and reliable manner Another object of the present invention is to provide a densitometer which has a simplified configuration and only requires a single degree of freedom in movement to measure a large number of specimens.

Another object of the present invention is to provide a densitometer which only has a single light source illuminated adjacent a single specimen at a given time for maximum reliability of optical density measurement.

Another object of the present invention is to provide a densitometer which simultaneously measures optical density of a large number of specimens and correlates optical density data for the plurality of specimens in an automatic fashion back to the individual specimens being measured.

Other further objects of the present invention will become apparent from a careful reading of the included drawing figures, the claims and detailed description of the invention.

BRIEF DESCRIPTION OF THE DRAWINGS

FIG. 1 is a schematic of a typical prior art densitometer system.

FIG. 2 is a perspective view of the densitometer of this invention utilizing LEDs and in use with a microtiter plate (MTP) containing multiple specimens within wells thereof.

DESCRIPTION OF THE PREFERRED EMBODIMENT

Figure 3:
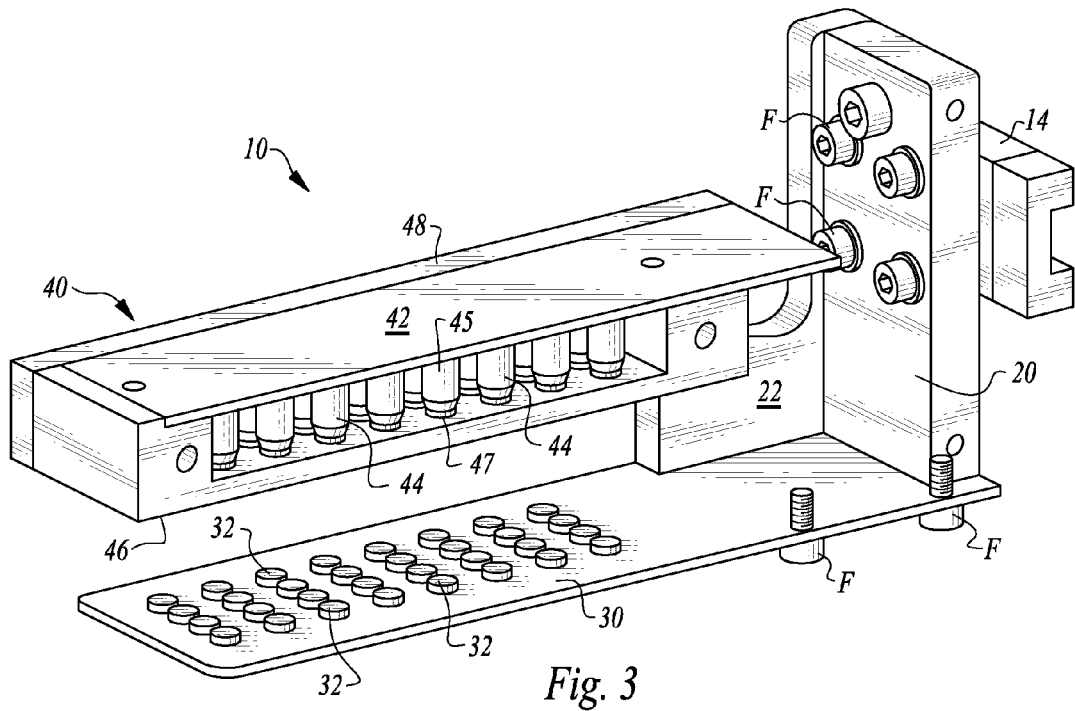
FIG. 3 is a perspective view of the LED densitometer of this invention shown alone, and with one wing portion thereof removed to illustrate interior details of the densitometer.

Referring to the drawings, wherein like reference numerals represent like parts throughout the various drawing figures, reference numeral 10 (FIGS. 2 and 3) is directed to an LED densitometer for use with a microtiter plate MTP or other specimen supporting structure. The densitometer 10 uses LEDs 44 some of which can emit light at a common frequency and others which emit light at differing frequencies, the different frequencies being selected to match frequencies desired in conducting optical density measurements according to known densitometry techniques.

In essence, and with particular reference to FIG. 3, basic details of the densitometer of this invention are described, according to a most preferred embodiment. In this embodiment, a mount wall 20 supports various portions of the densitometer 10 in a preferably substantially fixed manner. The mount wall 20 itself is movably carried through a carriage 14 upon a rail 12 (FIG. 2) so that the densitometer 10 has one degree of freedom of movement horizontally along a length of the rail 12, and relative to the microtiter plate MTP.

A detector plate 30 extends from the mount wall 20 beneath a gap in which the microtiter plate MTP is adapted to be positioned. This detector plate 30 includes a plurality of detectors 32 thereon. A housing 40 is provided parallel with the detector plate 30 and above the detector plate 30, and also mounted to the mount wall 20, such as through a pair of wings 22 (only one of which is shown in FIG. 3 for clarity, with both shown in FIG. 2). This housing 40 supports a plurality of LEDs 44 therein facing downwardly towards the detectors 32 of the detector plate 30. Each LED 44 is aligned with a detector 32. Spacing between the LEDs 44 and between the detectors 32 is similar to spacing between wells W in the microtiter plate MTP (FIG. 2).

Circuitry powers the LEDs 44 and the detectors 32 with the system programmed preferably to cause individual LEDs 44 to be sequentially powered to cause light emission at the desired frequency, and an associated measurement from an associated detector 32, for each position of the densitometer 10 relative to the microtiter plate MTP. The microtiter plate MTP can then be moved a distance of one well W spacing and the process repeated with the LEDs 44 aligned with next adjacent well W in the microtiter plate MTP, such that each of the specimens can have optical density measurements taken at each frequency available from the separate LEDs 44.

More specifically, and with continuing reference to FIGS. 2 and 3, details of the support system for the overall densitometer 10 are described. The densitometer 10 is simplified so that movement is only required in a single direction, horizontally along a long axis of the rail 12. This rail 12 is preferably a rigid substantially square elongate linearly extending structure which can be mounted to a wall or other support, preferably in a horizontal fashion. A carriage 14 is coupled to the rail 12 and is adapted to transit along a long axis of the rail 12 in a horizontal direction. Power supplied to the densitometer 10 would typically have appropriate slack and mounting to maintain electrical connection for all different positions of the densitometer 10 upon the rail 12. If the microtiter plate MTP has more columns of wells W than the housing 40 has LEDs, the microtiter plate MTP can be supported in a manner allowing it to be more perpendicular to the rail 12 so that specimens in wells can all be measured.

With continuing reference to FIGS. 2 and 3, details of the mount wall 20 are described according to a most preferred embodiment. The mount wall 20 is coupled to the carriage 14 and secures both the detector plate 30 or other lower structure with the housing 40 or other upper structure. This mount wall 20 is preferably a rigid mass secured to the carriage 14. The mount wall 20 is configured to support the detector plate 30 and housing 40 rigidly to the mount wall 20. For such attachment, most preferably a pair of wings 22 are mounted to edges of the mount wall 20. These wings 22 transition into arms 48 overlying a gap between the upper structure and lower structure of the densitometer 10.

With continuing reference to FIGS. 2 and 3, details of the detector plate 30, defining a preferred form of lower structure are described according to this preferred embodiment. The detector plate 30 is preferably in the form of a printed circuit board mounted directly to an underside of the mount wall 20 and to under portions of the wing 22 adjacent the mount wall 20. The detector plate 30 extends substantially horizontally away from the mount wall 20, with a long axis of the detector plate 30 substantially perpendicular to a long axis of the rail 12.

By configuring the detector plate 30 as a printed circuit board, the detectors 32 can be surface mounted on the printed circuit board and appropriate circuitry can be formed on the printed circuit board in the form of the detector plate 30. Such a structure minimizes mass of the lower structure in the form of the detector plate 30, minimizing forces associated with movement of the densitometer 10 along the rail 12.

The detectors 32 can be passive in that they do not require any power and generate a signal when light is incident upon the detectors 32. Alternatively, the detectors 32 can be of a type which are continuously powered and send an appropriate signal correlating with an amount of light incident thereon during operation of the densitometer 10.

Each of the detectors 32 have a particular address. A controller, such as in the form of a microprocessor is able to receive a signal from each detector 32 correlating with light intensity and from which optical density of a specimen can be calculated for a particular wavelength associated with the LED 44 associated with each detector 32. Such signals can be received from the detectors and then stored in a database associated with the microprocessor. This database can also include particular information relating to the specimen within the particular well of the microtiter plate MTP associated with the detector 32. The densitometer 10 can thus load data into this database relating to optical density of a specimen or array of specimens being examined.

While the lower structure is preferably in the form of a detector plate 30, it is conceivable that the detector plate 30 and housing 40 could be swapped so that the lower structure would in fact be the housing 40 supporting the LEDs 44 thereon. As another alternative, some other form of structure could be provided supporting the LEDs 44 and functioning as the lower structure of the densitometer 10.

With continuing reference to FIGS. 2 and 3, details of the housing 40 as a preferred form of upper structure, are described to this preferred embodiment. The housing 40 resides between two arms 48 extending from the wings 22. This housing 40 includes an upper plate 42 which is preferably in the form of a printed circuit board supporting the LEDs 44 thereon on an undersurface thereof. A support 46 is preferably provided which both holds the upper plate 42 at an upper portion of the housing 40, and also supports the LEDs 44 below the upper plate 42 and within the housing 40. This support 46 preferably has a plurality of openings therein with each opening aligned with one of the LEDs 44, so that the LEDs 44 can shine light down through the support 46 and toward the detectors 32. If desired, appropriate lenses or filters can be provided in these openings in the support 46 to focus the light and/or provide further filtering to keep the frequency of the light preferably between +5 and −5 nanometers of a desired frequency for measurement of optical density.

Each LED preferably has a base 45 mounted to the upper plate 42 and a tip 47 opposite the base 45 which is adjacent holes in the support 46. This base 45 of each LED 44 is preferably surface mounted on the upper plate 42 with the upper plate 42 in the form of a printed circuit board. Power to the printed circuit board and associated circuitry on the printed circuit board defining the upper plate 42 can send an appropriate driving signal to the LEDs 44, preferably sequentially in a manner directed by a microprocessor controller associated with the LEDs 44.

In a most preferred form of the invention, a program is executed to drive the LEDs 44 so that the LEDs 44 do not fire simultaneously, but rather sequentially for each position of the densitometer 10 relative to the microtiter plate MTP. With this firing sequence for the LEDs 44, optical density of each specimen is being read when only one LED 44 is illuminated and only one detector 32 associated with the illuminated LED 44 is generating an optical density correlated signal. In this way, the potential for a misreading due to light from other sources during detection is eliminated.

In the form of the invention particularly shown herein, the upper plate 42 includes a 4×8 array of LEDs 44. Eight LEDs 44 are provided in each column and with four rows of such columns. Each column of LEDs 44 preferably has a similar frequency of light emitted thereby. Each LED in a common row preferably has a different frequency of light emitted thereby. In this way, and with a 4×8 array of LEDs 44, eight specimens within eight separate wells W of the microtiter plate MTP can be substantially simultaneously analyzed. Furthermore, a total of thirty-two specimens can be analyzed at four frequencies. The densitometer 10 can then be advanced along the rail 12 one well W position, and the process repeated. Three-fourths of the wells will receive an additional optical density reading at a different frequency and a new column of wells W on the microtiter plate MTP will have a first set of data generated correlating with optical density. The densitometer 10 can then move ahead another well W position and again repeat this process.

At each position, the LEDs 44 and detectors 32 can rapidly detect optical density so that a data set is rapidly collected for a large number of specimens. The size of the microtiter plate MTP and the size of the arrays of LEDs 44 and detectors 32 could be adjusted up or down from this example. If the LEDs 44 have an undesirably long time required to illuminate and dissipate light from the LEDs, the firing pattern for the LEDs can be arranged so that LEDs 44 adjacent each other are not sequentially fired, but rather LEDs 44 having significant distance therebetween would be sequentially fired until all thirty-two LEDs 44 (in this example) have fired, so that the optical density readings can be obtained as quickly as possible while not affecting the quality of the optical density data being read.

While the densitometer 10 of this embodiment is shown with movement in a single direction, it is conceivable that a carrier for the densitometer 10 could facilitate movement of the densitometer 10 in two degrees of freedom perpendicular to each other and for a lesser number of LEDs 44 to be provided and/or a greater number of wells W within the microtiter plate MTP to be provided, and merely move the densitometer 10 in two mutually perpendicular directions, or the densitometer 10 in one direction and the microtiter plate MTP in one opposing direction, to gather the readings required for each of the specimens within the microtiter plate MTP.

Figure 4:
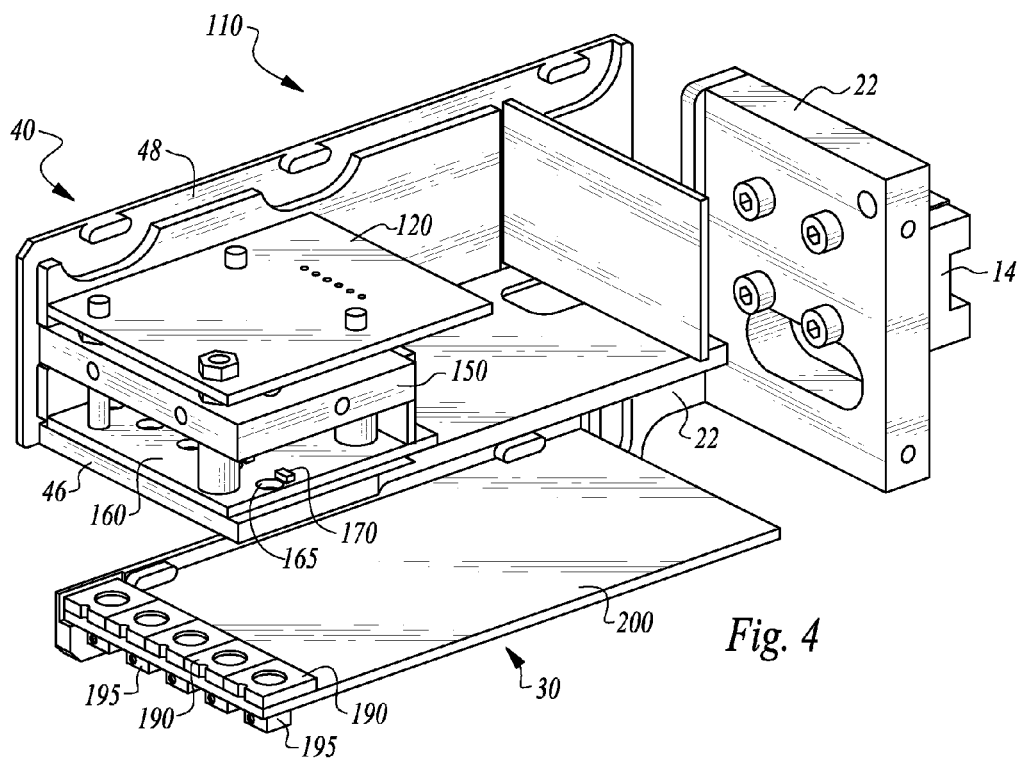
FIG. 4 is a perspective view of an alternative densitometer according to this invention.
Figure 5:
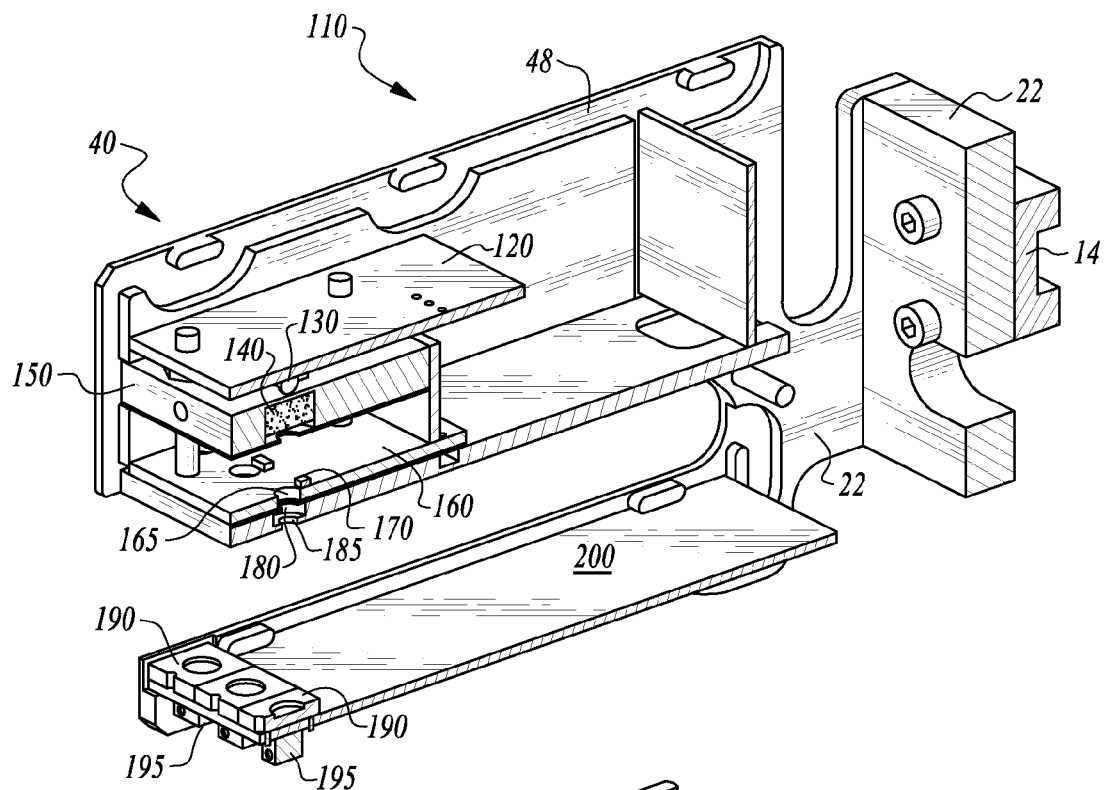
FIG. 5 is a perspective view of that which is shown in FIG. 4, and with portions cut away to reveal interior details.
Figure 6:
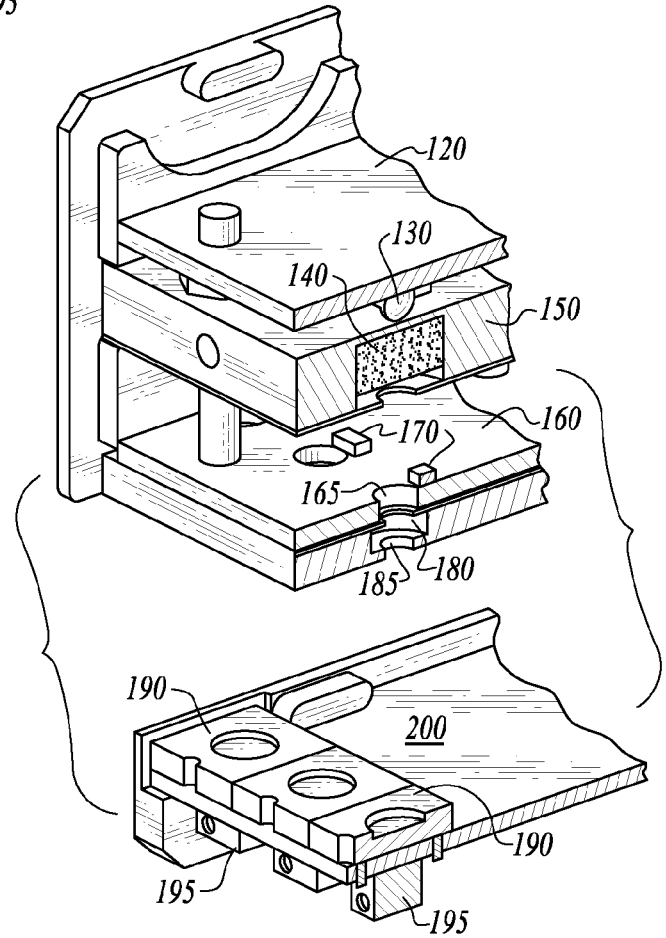
FIG. 6 is a detail of a portion of that which is shown in FIG. 5 illustrating details along a light path of the densitometer of the alternative embodiment of FIGS. 4 and 5.

FIGS. 4-6 show an alternative densitometer 110 provided according to this invention. With this alternative densitometer 110, rather than providing a two-dimensional array of LEDs, most preferably a single LED 130 is provided for each frequency of interest while as few as a single LED could conceivably be provided. In this particular example densitometer 110, five such LEDs 130 are provided. Details of the carriage of the alternative densitometer 110 are similar to those of the densitometer 10 described in detail above. However, the housing 40 (FIGS. 1-3) is slightly larger and interior details are modified somewhat. In particular, and within this larger housing 40, providing a preferred form of first structure for the densitometer 110, a pair of printed circuit boards are provided including an upper printed circuit board 120 and a middle printed circuit board 160.

LEDs 130 are surface mounted to the upper printed circuit board 120 with the LEDs 130 oriented to direct light downward from the upper printed circuit board 120. The upper printed circuit board 120 can be supported laterally adjacent the arm 48 of the housing 40. Furthermore, standoffs can be provided to space the upper printed circuit board 120 from the middle printed circuit board 160 and other structures within the housing 40.

Beneath the LED 130, preferably a block 150 is provided, such as a solid aluminum block. This block 150 includes a cavity 152 therein sized to receive a band pass filter 140 therein. This cavity 152 is accessed through an upper aperture 154 directly below the LED 130 and a lower aperture 156 at an end of the cavity 152 below the upper aperture 154 and on an opposite surface of the block 150 relative to the upper aperture 154.

The band pass filter 140 is preferably a filter of a type which only allows light of a particular narrow band of light frequencies to pass therethrough. In this way, an LED having a broader than desired bandwidth of frequencies can be utilized and still the densitometer 110 can focus on particular frequencies of interest when performing optical density measurements. Preferably, the singular block 150 includes multiple cavities 152, one cavity 152 for each of the five LEDs 130 shown in this particular embodiment of the densitometer 110. Five LEDs 130 are surface mounted on the upper printed circuit board 120 directing light down into a separate band pass filter 150 within the separate cavities 152 within the block 150. If an LED 130 is created or exists which has a narrow bandwidth of appropriate frequency, the band pass filter 140 could be omitted. Similarly, if the densitometer protocols do not require as specific and/or narrow a frequency, the filter 140 could be omitted. The filter 140 could also conceivably be integrated into the LED 130 itself.

A middle printed circuit board 160 is oriented substantially parallel with and below the upper printed circuit board 120 and below the block 150. The middle printed circuit board 160 has a hole 165 therein along a light path below the LED 130 and below the band pass filter 140, and aligned with the upper aperture 154 and lower aperture 156 adjacent the cavity 152 of the block 150. A photo detector 170 is preferably located adjacent this hole 165 in the middle printed circuit board 160. The photo detector 170 is adapted to measure intensity of light adjacent the hole 165 in the middle printed circuit board 160.

This light intensity is measured before the light has passed through a sample being measured by the densitometer 110. This photo detector 170 is preferably a portion of a feedback and control loop coupled to a power supply for an associated LED 130. The LED 130 is preferably configured within a circuit which can adjust power to the LED in a manner causing light intensity emitted by the LED to be increased or decreased. If the photo detector 170 detects light intensity passing through the hole 165 which is greater or less than desired, an appropriate control signal is fed back to the power supply for the associated LED 130 and modified so that the LED 130 will emit light at a desired and controlled intensity.

This feedback and control loop is important in that LEDs can vary in the amount of light intensity provided, and this variability can change with temperature and age of the LED, as well as other environmental factors. By providing this feedback and control loop associated with the photo detector 170, such variability in the LED is eliminated for reliable measurements by the densitometer 110.

A lens cavity 180 is provided below the hole 165 in the middle printed circuit board 160. This lens cavity 180 can support a lens above a lens aperture 185 formed in the support 46 of the housing 40. The lens within the lens cavity 180 preferably sufficiently focuses light from the LED 130 to cause the light to remain substantially as a column until it reaches the detector 190 on the lower printed circuit board 200 associated with the second structure of the densitometer 110 and similar to the lower plate 30 of the densitometer 10 described in detail above.

The detector 190 preferably is in the form of five detectors 190, one for each of the LEDs, and with each detector 190 having a variable resister 195 associated therewith for calibrating an operational range of the detectors 190 before their use. In particular, this variable resister 195 is configured so that it can be adjusted so that when no light absorbing objects are placed between the first structure and second structure, such a detector 190 is caused to be at an upper extent of its operational range from the pure light from the LED 130 striking the detector 190 without any absorption thereof. In this way, a maximum signal range can be obtained for each detector 190.

When sample supports such as microtiter plates MTP (FIG. 2) are utilized which have an array of wells W therein, the microtiter plate MTP or other sample support can be configured to control positioning of the microtiter plate MTP in an X direction, while the rail 12 and carriage 14 cause the densitometer 10, 110 to move in a Y direction. In this way, each LED of the alternate densitometer 110 can be positioned over each well W in a two-dimensional microtiter plate.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A densitometer for use with a sample support, the sample support including at least one sample support location adapted to hold a sample, each location formed of a location supporting material which is at least partially translucent, the densitometer comprising in combination:

a first structure adapted to reside on a first side of the sample support;

a second structure adapted to reside on a second side of the sample support spaced from said first side;

said first structure and said second structure spaced apart by a distance sufficient to allow the sample support to fit between said first structure and said second structure;

at least one of said first structure and said second structure including at least one LED thereon;

at least one of said first structure and said second structure including at least one detector thereon, said detector positioned to detect light from said LED after the light passes through a sample at the sample support location when the sample support is oriented between said first structure and said second structure;

wherein a plurality of LEDs are coupled to at least one of said first structure and said second structure;

wherein said plurality of LEDs include at least two LEDs spaced from each other a distance similar to a spacing between wells in the microtiter plate providing the sample support locations, and with which the densitometer is adapted to be used; and wherein said LEDs are coupled to a power source which supplies electric power to the LEDs to cause said LEDs to emit light, circuitry interposed between said power source and said LEDs provided to sequentially activate and deactivate individual LEDs, such that readings made by detectors result from illumination of only a single LED of known frequency.

2. The densitometer of claim 1 wherein said LEDs are adapted to emit light at different frequencies.

3. The densitometer of claim 1 wherein at least one of said LEDs shines light upon a band pass filter between said LED and said at least one detector, said band pass filter adapted to filter portions of light from said LED.

4. The densitometer of claim 3 wherein a photo detector is provided between said band pass filter and said at least one detector, said photo detector coupled to a feedback circuit adapted to at least partially control LED emitted light intensity, such that light from the LED is kept at a substantially constant luminosity.

5. The densitometer of claim 1 wherein a spacing of said plurality of LEDs from each other substantially equals spacing between wells of a microtiter plate having the at least one sample support location thereon, and with which the densitometer is adapted to be used.

6. The densitometer of claim 1 wherein said second structure includes a plurality of said detectors, each located substantially vertically spaced from said plurality of LEDs, with each of said plurality of detectors spaced apart by a distance similar to a spacing between said plurality of LEDs.

7. The densitometer of claim 1 wherein said plurality of LEDs are mounted upon a printed circuit board, said printed circuit board coupled to said first structure, with said plurality of LEDs facing downward from said first structure toward said second structure.

8. The densitometer of claim 7 wherein said plurality of detectors are each mounted upon a printed circuit board coupled to said second structure with said detectors facing said first structure with each of said detectors located substantially vertically beneath one of said plurality of LEDs.

9. The densitometer of claim 8 wherein said first structure and said second structure are adapted to be moved relative to the sample support such that different ones of said plurality of LEDs are aligned with different locations for sequential analysis of multiple locations on the sample support.

10. The densitometer of claim 9 wherein said plurality of LEDs are located in both a plurality of rows and a plurality of columns with said LEDs in a common column having a common frequency and said LEDs in common rows having distinct frequencies, and with said number of LEDs in said column matching a number of locations in the column of the sample support, said first structure and said second structure adapted to move in a single direction relative to said sample support such that each location of the sample support is sequentially aligned with one of said plurality of LEDs having different light frequencies while multiple locations in the sample support are analyzed for each position of said first structure and said second structure relative to the sample support.

11. A method for measuring optical density of a fluid, including the steps of:
providing a sample support including a plurality of sample support locations therein, said sample support formed of a material which is at least partially translucent;
locating at least one LED on a first side of said sample support;
locating at least one light detector on a second side of said sample support opposite said first side;
causing the LED to emit light including a desired frequency of light for optical density measurement;
measuring intensity of light transmitted through the specimen within the location of the sample support by the detector;
wherein said LED locating step includes locating a plurality of LEDs on a common structure spaced from each other a distance similar to a spacing between a plurality of the locations in the sample support, such that multiple LEDs are simultaneously aligned with multiple locations in the sample support; and
including the further step of repeating said causing step for individual LEDs sequentially and repeating said measuring step for a plurality of separate detectors sequentially, with one measuring step for each causing step, and the further step of correlating a signal generated by the detector with a position of a corresponding location in the sample support and a sample contained at that location, such that optical density measurements are correlated with a sample within the sample support which is being analyzed.

12. The method of claim 11 wherein said plurality of LEDs include at least two LEDs emitting light at different frequencies.

13. The method of claim 12 including the further step of configuring the plurality of LEDs to be in an array of LEDs in rows of differing frequencies and columns of similar frequencies, and configuring the sample support to include a plurality of locations within an array having at least as many rows of locations and at least as many columns of locations as a number of LEDs in rows and LEDs in columns.

14. The method of claim 11 wherein said locating at least one light detector step includes positioning a plurality of detectors on a common structure, each of the detectors aligned with one of the plurality of LEDs.

15. The method of claim 11 including the further step of moving the at least one LED and the at least one detector together after said measuring step to align the LED and the detector on opposite sides of a different location on the sample support.

16. An LED densitometer, comprising in combination:
a first structure adapted to be located adjacent a sample;
a second structure adapted to be located adjacent the sample and on a side of the sample substantially opposite said first structure;
at least one LED coupled to one of said first structure and said second structure;
said LED having a spectrum of light emitted therefrom that includes a frequency useful in measuring optical density of the sample;
a detector coupled to one of said first structure and said second structure;

said detector adapted to detect the frequency of light emitted by said at least one LED;

wherein said first structure and said second structure are fixed to each other, at least indirectly;

wherein at least one of said first structure and said second structure includes a plurality of LEDs thereon and at least one of said first structure and said second structure includes a plurality of detectors thereon, each said detector positioned to detect light from a different one of said plurality of LEDs, said plurality of LEDs spaced apart by a distance similar to a spacing between a plurality of samples on a sample support adapted to be positioned between said first structure and said second structure;

wherein a gap between said first structure and said second structure is sized to receive the sample support in the form of a microtiter plate therebetween having a plurality of wells therein each of said wells adapted to support a separate sample, and with LED spacing of said plurality of LEDs substantially equal to well spacing in the microtiter plate; and wherein said plurality of LEDs are coupled to a power source through electric circuitry, said circuitry configured to power said LEDs sequentially, one at a time.

17. The LED densitometer of claim 13 wherein at least two of said plurality of LEDs provide light at different frequencies from each other.

18. The LED densitometer of claim 16 wherein said first structure and said second structure are fixed together and to a common movable support, said movable support adapted to move said first structure and said second structure together relative to said microtiter plate.

19. The LED densitometer of claim 18 wherein said plurality of detectors are coupled to a microprocessor supporting a database adapted to store optical density measurements correlating with an optical density signal generated by said plurality of detectors, and correlating said measurements with particular wells of said microtiter plate and specific LEDs corresponding with said detectors.

20. The LED densitometer of claim 16 wherein at least one of said LED shines light upon a band pass filter between said LED and said at least one detector, said band pass filter adapted to filter portions of light from the LED.

21. The LED densitometer of claim 20 wherein a photo detector is provided between said band pass filter and said at least one detector, said photo detector coupled to a feedback circuit adapted to at least partially control LED emitted light intensity.

* * * * *